(12) United States Patent
Schlienger et al.

(10) Patent No.: US 8,109,930 B2
(45) Date of Patent: *Feb. 7, 2012

(54) SURGICAL NAIL

(75) Inventors: Andrè Schlienger, Münchenstein (CH);
Markus Buettler, Oensingen (CH);
Peter Senn, Waldenburg (CH)

(73) Assignee: Synthes USA, LLC, West Chester, PA (US)

( * ) Notice: Subject to any disclaimer, the term of this patent is extended or adjusted under 35 U.S.C. 154(b) by 902 days.

This patent is subject to a terminal disclaimer.

(21) Appl. No.: 11/630,726

(22) PCT Filed: Jun. 23, 2004

(86) PCT No.: PCT/CH2004/000381
§ 371 (c)(1),
(2), (4) Date: Jun. 19, 2008

(87) PCT Pub. No.: WO2006/000108
PCT Pub. Date: Jan. 5, 2006

(65) Prior Publication Data
US 2008/0255558 A1 Oct. 16, 2008

(51) Int. Cl.
*A61B 17/56* (2006.01)
(52) U.S. Cl. .......................................... 606/62

(58) Field of Classification Search ............. 606/62–68, 606/60, 329
See application file for complete search history.

(56) References Cited

U.S. PATENT DOCUMENTS

| | | | | |
|---|---|---|---|---|
| 4,970,570 | A | * | 11/1990 | Agarwala et al. ............. 257/735 |
| 5,281,222 | A | * | 1/1994 | Allard et al. .................... 606/54 |
| 5,365,736 | A | * | 11/1994 | Yamamoto ....................... 60/413 |
| 6,183,022 | B1 | * | 2/2001 | Guest ............................ 285/322 |
| 6,296,645 | B1 | | 10/2001 | Hover et al. |
| 6,808,527 | B2 | * | 10/2004 | Lower et al. .................... 606/62 |
| 7,247,157 | B2 | | 7/2007 | Prager et al. |
| 2002/0103488 | A1 | | 8/2002 | Lower et al. |
| 2002/0147454 | A1 | * | 10/2002 | Neto .............................. 606/73 |
| 2003/0171754 | A1 | | 9/2003 | Del Medico |
| 2005/0033289 | A1 | * | 2/2005 | Warren et al. ................... 606/53 |

FOREIGN PATENT DOCUMENTS
DE 20300987 5/2003
WO WO 2004/096067 A2 11/2004

* cited by examiner

*Primary Examiner* — Pedro Philogene
(74) *Attorney, Agent, or Firm* — Fay Kaplun & Marcin, LLP

(57) ABSTRACT

An intramedullary nail comprising a central axis and a transverse borehole, provided with an insert which can be introduced into the transverse borehole, said insert also containing a longitudinal slit.

28 Claims, 5 Drawing Sheets

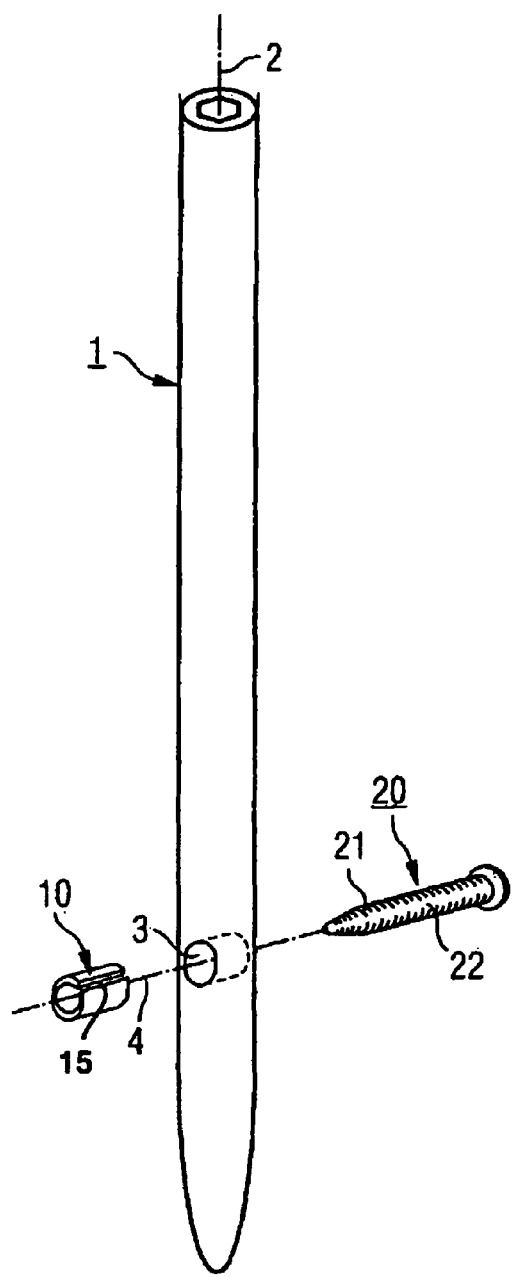
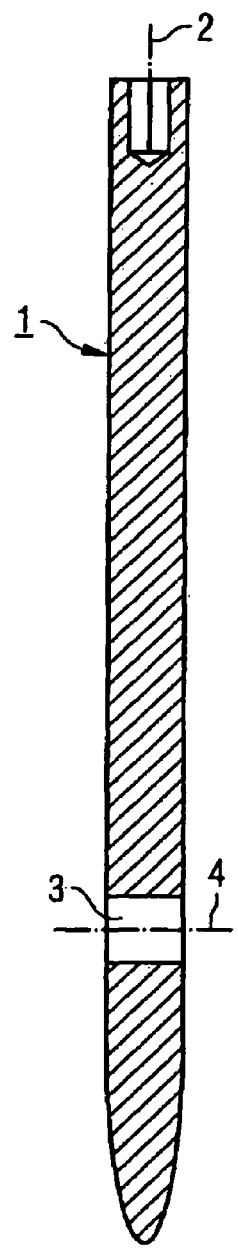
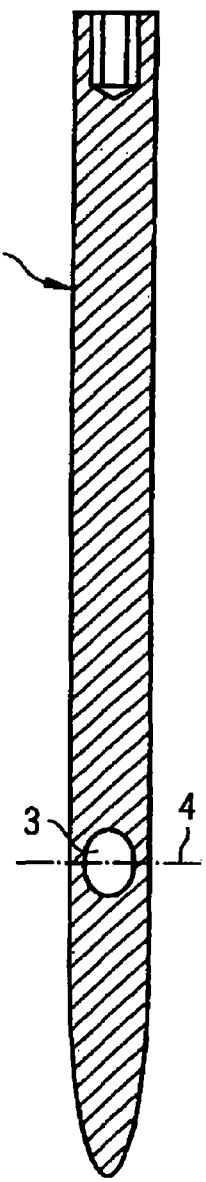

SURGICAL NAIL

This application is a national stage application of PCT/CH2004/000381, filed Jun. 23, 2004.

FIELD OF THE INVENTION

The invention relates to a surgical nail, in particular an intramedullary nail comprising a transverse bore and an insert insertable into the transverse bore.

BACKGROUND OF THE INVENTION

The securing function of intramedullary nails is already known in the state of the art. The locking screws or locking pins (hereinafter only the term "locking screw" is used, but this is also intended to include the term "locking pins") are inserted into the transverse bores in an intramedullary nail either with the help of an imaging method (x-ray monitoring) or a more or less complex target device. In both cases, a certain target inaccuracy is unavoidable, i.e., the tip of the screw cannot be precisely aligned coaxially with the central axis of the transverse bore but instead deviates therefrom by a certain amount. In order for the locking screw to open into the transverse bore and in order for it to be passed through this bore despite this target error, the outside diameter of the screw is undersized in relation to the diameter of the transverse bore. If the target inaccuracy remains within the scope of this undersizing, then the locking screw can be passed through the transverse bore with no problem despite this target error. However, the locking screw has a certain play in relation to the transverse bore, because of the undersizing.

This play defines the amount by which the main bone fragments, which are to be secured in the corresponding locking hole by means of locking screws, are able to move in relation to the nail and thus also, owing to the rigidity of the nail, in relation to other main bone fragments secured using the same nail. To ensure the applicability of this locking means for the surgeon, this play is unavoidable but nevertheless undesirable clinically for certain indications (e.g., in the case of metaphyseal fragments).

Even nails having a solid cross section, which may have an inside thread in the locking hole, are not free of play. The inside thread only prevents the nail from being axially displaceable on the locking screw.

U.S. Pat. No. 6,296,645 HOVER ET AL. describes a hollow intramedullary nail made of metal having one or two plastic inserts in the jacket openings in the transverse bore that are positioned diametrically opposite one another and are referred to as windows, the locking screw being insertable through these plastic inserts. One disadvantage of this known intramedullary nail is the fact that the window-like plastic inserts can easily be pushed in, which causes the desired function to be lost. However, even with very cautious manipulation, the two plastic inserts could be forced out of their "window" in pushing the locking screw through, which would also lead to a loss of function.

SUMMARY OF THE INVENTION

The present invention attempts to find a remedy to this situation. The object of the invention is to create a surgical nail, in particular an intramedullary nail, with which the play prevailing between it and the locking screw can be eliminated at no risk and an improved holding power and an improved guidance effect between the locking screw and the intramedullary nail can be achieved.

The invention solves this problem with a surgical nail, in particular an intramedullary nail, comprising a central axis and at least one transverse bore having a transverse axis running across the central axis, and comprising an insert with a longitudinal axis insertable into the transverse bore, wherein the insert has a longitudinal slot and is essentially congruent with the transverse bore.

The following advantages can be achieved in this way:

a) the target accuracy in introducing the locking screw is unimpaired;

b) the physician can still choose intraoperatively whether or not to achieve a stable-angle locking of the locking screw, where the term "stable-angle" means a restriction of certain degrees of freedom;

c) the possibility of stable-angle fixation of the bone fragment in certain directions for a certain amount of the load and d) the nail and insert may be sterile packaged separately and the surgeon may select whether to use the nail with or without an insert. In the former case, the surgeon may insert the insert itself into the transverse bore in the nail and optionally remove it again. If the surgeon uses the nail without an insert, the latter remains in the sterile package for the next use.

In a special embodiment, the insert may be provided with an outside thread for at least a portion. The longitudinal slot preferably runs continuously over the entire length of the insert. The insert may also have several longitudinal slots that do not run over the entire length of the insert, resulting in an increased flexibility of the insert. The longitudinal slots may also be arranged so they are offset on the circumference of the insert or situated axially one above the other.

The nail is preferably made of a material "M" having the tensile strength $F_z$, the compressive strength $F_d$, the density $\rho_2$ and the modulus of elasticity E, and the insert is advantageously made of a material "m" which has a lower modulus of elasticity e<E than the material M.

Preferably the insert is designed to be essentially congruent with the transverse bore in the nail.

The insert may have a bore that is coaxial with its longitudinal axis, the longitudinal slot optionally communicating with this coaxial bore.

The modulus of elasticity "e" of the insert advantageously amounts to e<0.8E, preferably e<0.7E.

The material "m" of the insert preferably has the tensile strength $f_z<F_z$ and the compressive strength $f_d<F_d$.

The material "m" of the insert may be made of a biocompatible plastic, preferably a polyethylene or a high-molecular-weight polyethylene (HMWPE). These materials have the advantage that there is no degradation of the plastic, yielding unknown degradation products. The plastic may also be a bioabsorbable polymer or copolymer, preferably a polylactide. In this embodiment, there initially results a play-free transverse locking of the intramedullary nail which is then gradually reversed with increasing absorption of the polymer so the transverse locking screw becomes mobile again in relation to the intramedullary nail and thus the bone fragments thereby treated also become mobile again. This allows dynamic motion of bone fragments after successful fracture consolidation. The bioabsorbable material has the advantage that the chips formed in cutting the thread of the locking screw through the insert can be degraded by the patient's body. Another advantage is the possibility of achieving a different strength of stable-angle locking of the locking screw over time, i.e., achieving a gradual reduction in holding power.

The transverse bore may be a circular bore, whereby in this case the cross-sectional profile F has the maximum lengths a=b. However, it may also be designed as an elongated hole where the cross-sectional profile F has the maximum lengths a>b.

The material "m" of the insert advantageously has a lower density $\rho_1$ than the material M with the density $\rho_2$, where it preferably holds that $\rho_1 < 0.8\, \rho_2$.

When using the nail as a locking nail, it has a locking screw or a locking pin that can be inserted into its transverse bore through the insert, its shaft having a diameter "d" which obeys the conditions a>d<b. The transverse bore may become wider toward the surface of the nail, preferably in the form of a conical section. This has the advantage that an insert having a corresponding conical section inserted therein cannot be displaced axially any further in the insertion direction.

For the locking screw to be used with the nail, comprising a shaft with an outside thread, the diameter "d" of the outside thread is preferably a>d<b and "d" is preferably at least 5% less than the smaller of the two dimensions a and b.

In another embodiment, the insert may comprise a pin having a head with a conical enlargement. The insert may also comprise a pin having a central bore and a plurality of conical enlargements which are arranged on the periphery and are able to engage in corresponding cavities and/or in the longitudinal bore in the nail in the area of the transverse bore in the form of a click closure.

BRIEF DESCRIPTION OF THE DRAWINGS

Invention and refinements of the invention are described in greater detail below on the basis of the partially schematic diagrams of several exemplary embodiments.

They show:

FIG. 1 a perspective view of a through-cannulated intramedullary nail with a transverse bore and an insert fitting thereto plus a transverse locking screw;

FIG. 2 a longitudinal section through the intramedullary nail according to FIG. 1;

FIG. 3 a longitudinal section through the intramedullary nail according to FIG. 1, rotated 90°;

DETAILED DESCRIPTION

Figure 4:
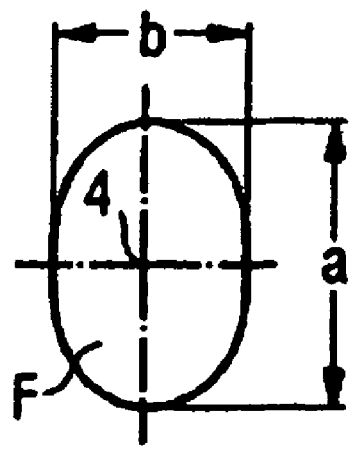
FIG. 4 an enlarged schematic view of the profile of the transverse bore of the intramedullary nail according to FIG. 1.

The surgical nail 1 shown in FIGS. 1 through 3 is an intramedullary nail for tubular bones having a central axis 2 made of a metal or a metal alloy, i.e., a material having a relatively high strength (tensile strength $F_z$, compressive strength $F_d$ and modulus of elasticity E). The nail 1 has a transverse bore 3 with the transverse axis 4, designed as an elongated hole having the cross-sectional profile F running across the central axis 2. As shown in FIG. 4, the transverse bore 3 has a cross-sectional profile F which has a maximum length a in the direction of the central axis 2 and a maximum width b perpendicular thereto. The nail may also have other transverse bores 3 (round or oval) (not shown in the drawing).

As also shown in FIG. 1, a hollow insert 10 is provided for insertion into the transverse bore 3 and has a continuous longitudinal slot 15. The dimensioning of the insert 10 is congruent with that of the transverse bore 3 and/or is selected, so that when inserted, a press-fit is obtained, thereby preventing the insert 10 from falling out of the transverse bore 3. The insert 10 is made of a material "m" having a lower strength, in particular a lower modulus of elasticity (in comparison with the material M of the intramedullary nail).

Figure 5:
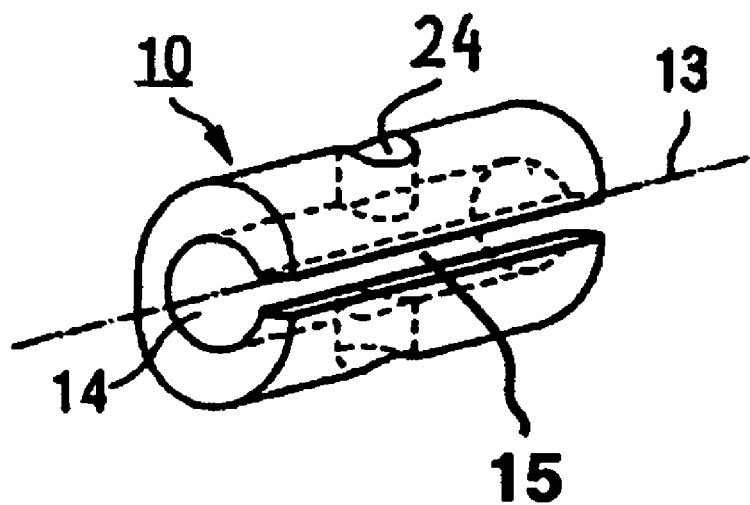
FIG. 5 a one-piece insert having a transverse bore which is approximately aligned with the nail cannulation after being inserted.

As shown in FIG. 5, the insert 10 has a coaxial longitudinal bore 14 with its longitudinal axis 13 and a transverse bore 24 corresponding to its cannulation and perpendicular thereto after insertion into the intramedullary nail.

Figure 10:
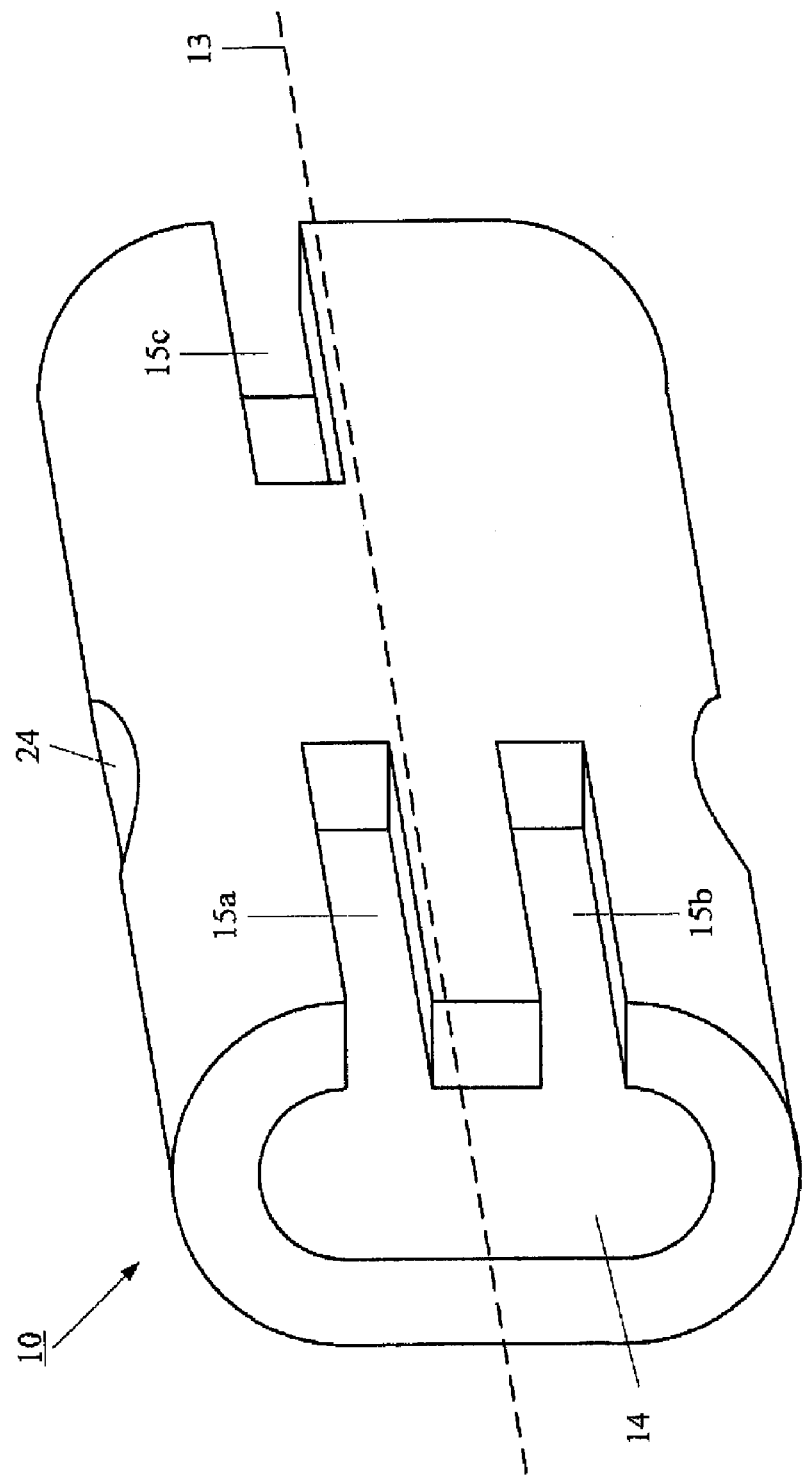
FIG. 10 shows a one-piece insert having a transverse bore which is approximately aligned with the nail cannulation after being inserted with several longitudinal slots.

As shown in FIG. 10, the insert 10 has a coaxial longitudinal bore 14 with its longitudinal axis 13 and a transverse bore 24 corresponding to its cannulation and perpendicular thereto after insertion into the intramedullary nail. In contrast to FIG. 5, more than one longitudinal slot 15a, 15b, and 15c may be disposed in which each of the longitudinal slots 15a, 15b, and 15c do not run over the entire length of the insert. Furthermore, FIG. 10 illustrates that the longitudinal slots may be offset from each other on the circumference of the insert 10 (e.g., longitudinal slots 15a, 15b), situated axially one above the other (e.g., longitudinal slots 15a, 15c), or a combination thereof.

Figure 6:
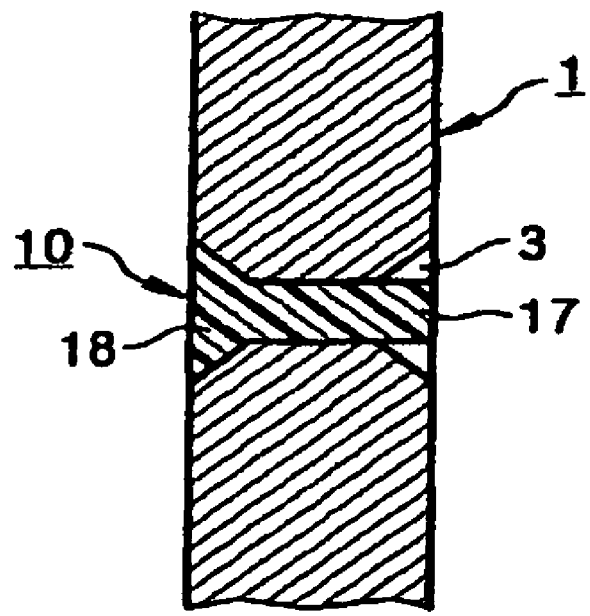
FIG. 6 a partial longitudinal section through another modified intramedullary nail having a modified one-piece insert.

FIG. 6 shows a variant of a one-piece insert 10 comprising a pin 17 having a conical enlarged head 18 which may be inserted into a suitably designed transverse bore 3 of the nail 1.

Figure 7:
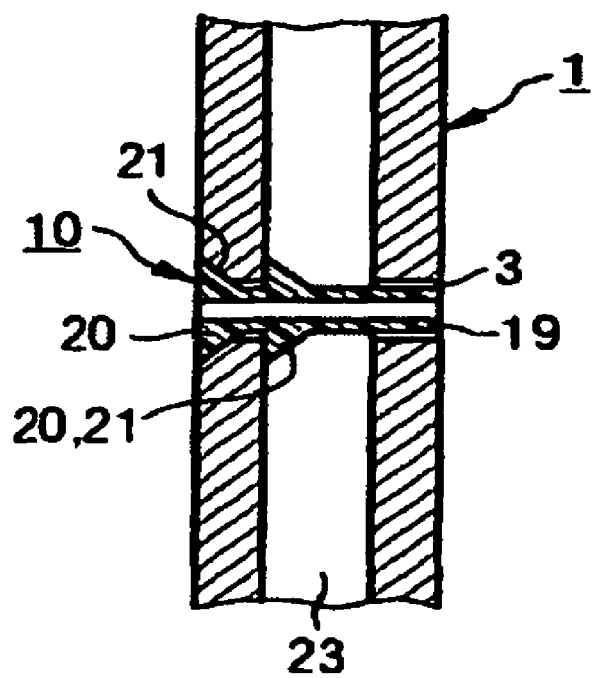
FIG. 7 a partial longitudinal section through another modified intramedullary nail having a modified one-piece insert.

FIG. 7 shows another variant of the one-piece insert 10 consisting of a pin 19 having a central bore through it with multiple peripheral conical enlargements 20 arranged on the periphery and able to engage in corresponding cavities 21 and/or in the longitudinal bore 23 of the nail 1 in the area of the transverse bore 3 in the form of a click closure. To this end, the transverse bore 3 of the nail 1 is adapted geometrically accordingly.

Figure 8:
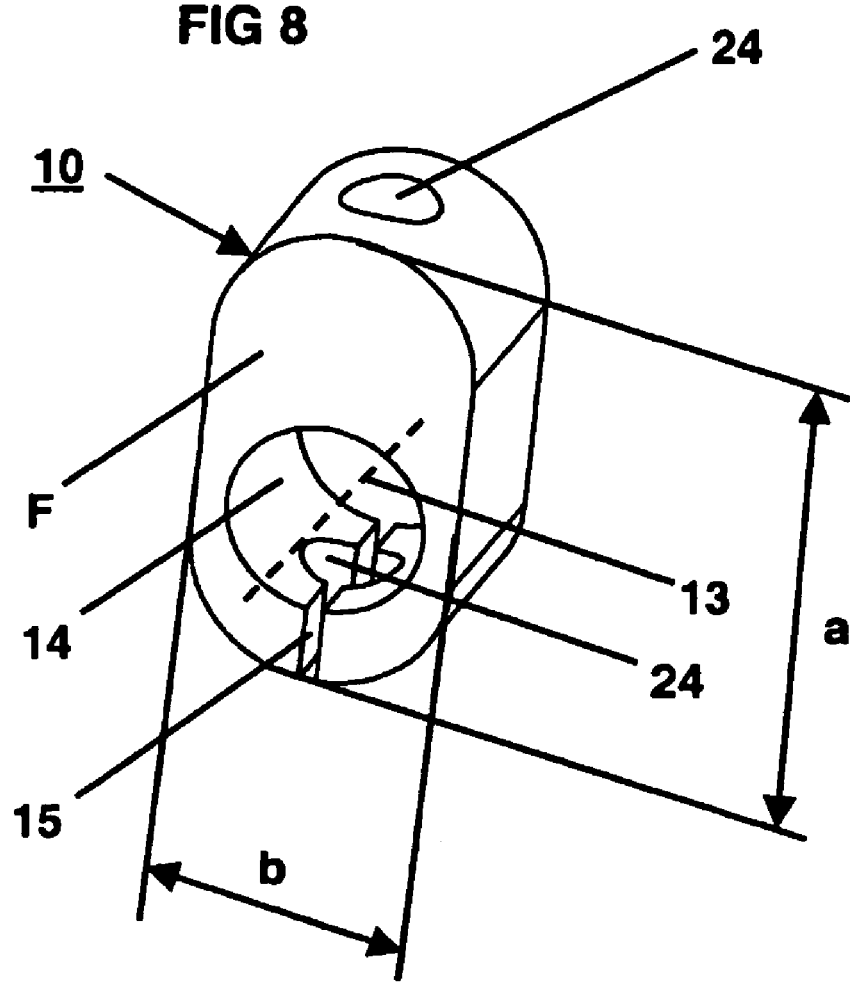
FIG. 8 a perspective view of a modified insert for an elongated hole transverse bore, and FIG. 9 a perspective view of a modified insert for a normal circular cylindrical transverse bore.

FIG. 8 shows another variant of an insert 10 for an elongated hole transverse bore.

The longitudinal bore 14 and the parallel longitudinal slot 15 communicate with one another. Instead of a decentralized arrangement of the longitudinal bore 14, a central arrangement may also be selected. By analogy with the variant according to FIG. 5, the insert 10 has a corresponding bore 24 perpendicular to its cannulation after insertion into the intramedullary nail.

Figure 9:
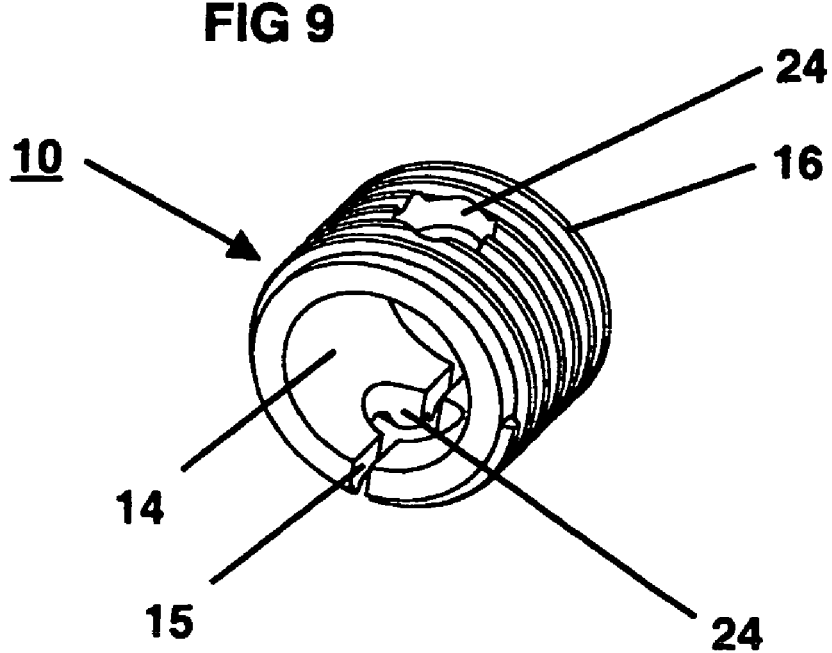

FIG. 9 shows another variant of an insert 10 for a normal circular cylindrical transverse bore 3 in a nail 1. The longitudinal bore 14 and the parallel longitudinal slot 15 communicate with one another. The insert 10 has an outside thread 16 on its outer lateral surface, preferably corresponding to an inside thread created in the transverse bore 3 in the nail 1. As in the variant according to FIG. 5, the insert 10 has a corresponding transverse bore 24 perpendicular to its cannulation after insertion into the intramedullary nail.

The invention claimed is:

1. An intramedullary nail, comprising:
    a central axis;
    at least one transverse bore extending across the central axis, having a length, a transverse axis, and a cross-sectional profile F with maximum dimension "a" in the direction of the central axis and a maximum dimension "b" perpendicular thereto; and an insert having a length, a longitudinal axis, and a longitudinal slot, the insert being insertable into the transverse bore and essentially congruent with the transverse bore, the longitudinal slot being configured so that the insert is press-fit into the transverse bore to prevent the insert from falling out of the transverse bore.

2. The intramedullary nail of claim 1, wherein the length of the insert is substantially the same as the length of the transverse bore.

3. The intramedullary nail of claim 1, wherein the outside of the insert is at least partially threaded.

4. The intramedullary nail of claim 1, wherein the longitudinal slot extends along the entire length of the insert.

5. The intramedullary nail of claim 1, wherein the insert has several longitudinal slots, each longitudinal slot extending along only part of the length of the insert.

6. The intramedullary nail of claim 5, wherein the longitudinal slots are offset from each other.

7. The intramedullary nail of claim 5, wherein the longitudinal slots are arranged axially one above the other.

8. The intramedullary nail of claim 1, wherein the intramedullary nail is made of a material M having a tensile strength $F_2$, a compressive strength $F_d$, a density $\rho_2$ and a modulus of elasticity E, and wherein the insert is made of a material m which has a lower modulus of elasticity e<E than the material M.

9. The intramedullary nail of claim 8, wherein e<0.8 E.

10. The intramedullary nail of claim 9, wherein e<0.7 E.

11. The intramedullary nail of claim 1, wherein the insert comprises a coaxial bore coaxial with its longitudinal axis.

12. The intramedullary nail of claim 11, wherein the longitudinal slot communicates with the coaxial bore.

13. The intramedullary nail of claim 1, wherein the transverse bore is unthreaded.

14. The intramedullary nail of claim 1, wherein the transverse bore has a smooth inner surface.

15. The intramedullary nail of claim 8, wherein the material m is a biocompatible plastic, preferably a polyethylene or a high-molecular-weight polyethylene (HMWPE).

16. The intramedullary nail of claim 15, wherein the plastic is a bioabsorbable polymer or copolymer.

17. The intramedullary nail of claim 16, wherein the plastic is a polyactide.

18. The intramedullary nail of claim 1, wherein the transverse bore is a substantially circular bore, such that dimensions "a" and "b" of cross-sectional profile F are substantially equal.

19. The intramedullary nail of claim 1, wherein the transverse bore is an elongated bore, such that dimensions "a" and "ab" of cross-sectional profile F are not equal.

20. The intramedullary nail of claim 8, wherein the material m has a lower density $\rho_1$ than the density $\rho_2$ of the material M.

21. The intramedullary nail of claim 20, wherein $\rho_1$ <0.8 $\rho_2$.

22. The intramedullary nail of claim 1, comprising a locking screw or a locking pin insertable into the transverse bore through the insert, the shaft thereof having a diameter "d" which obeys the conditions a>d<b.

23. The intramedullary nail of claim 1, wherein the transverse bore widens toward the surface of the nail, in the form of a conical section.

24. The intramedullary nail of claim 1, further comprising a locking screw having a shaft and an outside thread, the outside thread having a diameter "d" such that a>d<b.

25. The intramedullary nail of claim 24, wherein "d" is at least 5% smaller than the smaller of "a" and "b."

26. The intramedullary nail of claim 23, wherein the insert consists of a pin with a conically enlarged head.

27. An intramedullary nail, comprising:
a central axis;
a central bore coaxial with the central axis;
at least one transverse bore extending across the central axis, having a length and a transverse axis; and
an insert insertable into the transverse bore, consisting of a pin having a central bore and one or more conical enlargements which are able to engage the nail in the form of a click closure, one conical enlargements engaging the central bore.

28. The intramedullary nail of claim 27, wherein one of the one or more conical enlargements engages a conical cavity in the nail.

* * * * *